United States Patent [19]

Brakel et al.

[11] Patent Number: 5,082,830
[45] Date of Patent: Jan. 21, 1992

[54] END LABELED NUCLEOTIDE PROBE

[75] Inventors: Christine L. Brakel, Brightwaters, N.Y.; Alan F. Cook, Cedar Groove, N.J.; Edmund Vuocolo, Bronx, N.Y.

[73] Assignee: Enzo Biochem, Inc., New York, N.Y.

[21] Appl. No.: 160,607

[22] Filed: Feb. 26, 1988

[51] Int. Cl.⁵ .................. A61K 31/70; C07H 15/12; C12Q 1/68; C12P 19/34
[52] U.S. Cl. ....................... 514/44; 536/27; 435/6; 435/91
[58] Field of Search .................. 536/27; 514/44

[56] References Cited

U.S. PATENT DOCUMENTS 4,760,017  7/1988  McCormick ................ 435/6

FOREIGN PATENT DOCUMENTS 0122614  10/1984  European Pat. Off. ............ 1/68
0251283   1/1988  European Pat. Off. ............ 1/68
60-256059  5/1986  Japan .......................... 1/68

OTHER PUBLICATIONS

Chem. Absts. 110(11):91667b, 1989.
Agrawal et al., Nuc. Ac. Res. 14(15):6277-6245, 1986.
Kempe et al., Nuc. Ac. Res. 13(1):45-57, 1985.
Leary et al., PNAS 80:4045-4049, 1983.
Cook, et al., "Synthesis and Hybridization of a Series of Biotinylated Oligonucleotides", Nucleic Acids Research vol. 16, No. 9, (pp. 4079-4093) (1988).
Langer-Safter et al., *PNAS* 79:4381 (1982).
Langer et al., *PNAS* 78:6633 (1981).
Brakel et al., in Kingsbury et al. (Eds.) Rapid Detection and Identification of Infectious Agents, Academic Press, New York, pp. 235-243 (1985).
Riley et al., *DNA* 5:333 (1986).
Forster et al., *Nuc. Ac. Res.* 13:745 (1985).
Chollet et al., *Nuc. Ac. Res. 13:1529 (1985).*
Wachter et al., *Nuc. Ac. Res.* 14:7985 (1986).
Chu et al., *DNA* 4:327 (1985).
Bryan et al., *DNA* 3:124 (1984).
Murasugi et al. *DNA* 3:269 (1984).
Haralambidis, et al., *Nucleic Acids Research* 15(12):4857-4876 (1987).

Primary Examiner—John W. Rollins
Attorney, Agent, or Firm—Serle I. Mosoff; Ronald C. Fedus

[57] ABSTRACT

An oligo- or polynucleotide having at least one biotin directly or indirectly attached to each of the 5' and 3' end nucleotides thereof and a nucleic acid hybridization assay system for use therewith. The biotins are optionally attached through linkage groups that do not interfere with hybridization. The biotins can further serve to attach a biotinylated polymer.

32 Claims, 3 Drawing Sheets

END LABELED NUCLEOTIDE PROBE

BACKGROUND OF THE INVENTION

1. Field of the Invention

This invention relates to signal generating systems for specific binding assays. More particularly, it relates to improvements in the labeling of nucleic acid hybridization assay probes with nonradioactive moeities, such as biotin and other known labeling moieties.

2. Brief Description of the Prior Art

Oligonucleotides, including oligodeoxynucleotides, (oligomers) are now widely used as probes for the detection of specific genes and other nucleic acid sequences. The most common method for the labeling of oligonucleotides has been the incorporation of the isotope $^{32}P$. While this approach is suitable for research purposes, the safety precautions required, together with the relatively short half life of $^{32}P$ have stimulated the search for effective, non-radioactive labeling methods.

Among the variety of non-radioactive labels thus far reported, the vitamin biotin (and biotin analogues such as iminobiotin) has attracted considerable attention due to its high affinity binding with avidin and streptavidin, versatility, and ease of handling, in addition to the sensitivity of the detection systems in which it is used. Biotinylated probes have been used for the sensitive colorimetric detection of target nucleic acid sequences on nitrocellulose filters, as shown in Leary, et. al., PNAS 80:4045(1983), and for in situ detection of target DNAs, as in Langer-Safer, et. al., PNAS, 79:4381(1982).

The enzymatic incorporation of biotin into DNA is well documented; incorporation of a biotinylated nucleoside triphosphate can be accomplished by nick translation procedures, as discussed in Langer, et. al., PNAS 78:6633(1981), or by terminal addition with terminal deoxynucleotide transferase, as described by Brakel, et. al., in Kingsbury, et. al. (Eds.), Rapid Detection and Identification of Infectious Agents, Academic Press, New York, pgs. 235-243(1985) and in Riley, et. al., DNA, 5:333(1986). Biotin labels have also been introduced into DNA using a photochemical method. See, for example, Forster, et. al., Nuc. Ac. Res., 13:745(1985).

Several groups have concentrated on the development of methods for the attachment of a single biotin at the 5'-end of an oligonucleotide, either via a phosphoramidate, as in Chollet, et. al., Nuc. Ac. Res., 13:1529(1985) and in Wachter, et. al., Nuc. Ac. Res., 14:7985(1986), or a phosphodiester linkage. Regarding the latter, see Kempe, et. al., Nuc. Ac. Res., 13:45(1985); Agrawal, et. al., Nuc. Ac. Res., 14:6227(1986); and Chu, et. al., DNA, 4:327(1985). Although these methods can be used to provide oligonucleotide probes, only one biotin group per oligomer is introduced by these methods.

In order to increase the sensitivity of biotinylated oligonucleotide probes, efforts have been directed to the introduction of several biotins in such a way that the hybridization of the oligomer is not impaired. This has been accomplished by enzymatic methods, using terminal transferase, as in Riley, et. al., supra, or Klenow fragment, as in Murasugi, et. al., DNA, 3:269(1984). Also, chemical procedures for the introduction of multiple biotins on sidearms attached to internal nucleotides of a probe have been described in a preliminary report by Bryan, et. al., DNA, 3:124(1984).

SUMMARY OF THE INVENTION

The present invention provides end labeled, particularly end biotinylated, nucleotides which are useful as components of nucleic acid hybridization assays. Particularly, the novel compounds described enhance the signal generating output of polynucleotide and deoxypolynucleotide probes whereby the assays utilizing such probes are made more sensitive.

Accordingly, the principal aspect of the present invention provides a novel compound comprising an oligo- or polynucleotide having at least one biotin or other nonradioactive detection moiety directly or indirectly attached to each of the 5' and 3' end nucleotides or end nucleotide regions thereof and a nucleic acid hybridization assay system and method which include and use the novel compound.

In one aspect, at least one of the biotins is attached through a linkage group that does not interfere with hybridization. In another aspect, at least one of the end nucleotides is attached to a polybiotinylated polymer. In still another aspect of the invention, the novel oligomer is synthesized from nucleotide phosphoramidates having a functional group attached to the 5-position of the pyrimidine ring. The nucleic acid hybridization assay composition comprising an oligo- or polynucleotide of the invention can further include additional reagents.

DETAILED DESCRIPTION OF PREFERRED EMBODIMENTS

Figure 1:
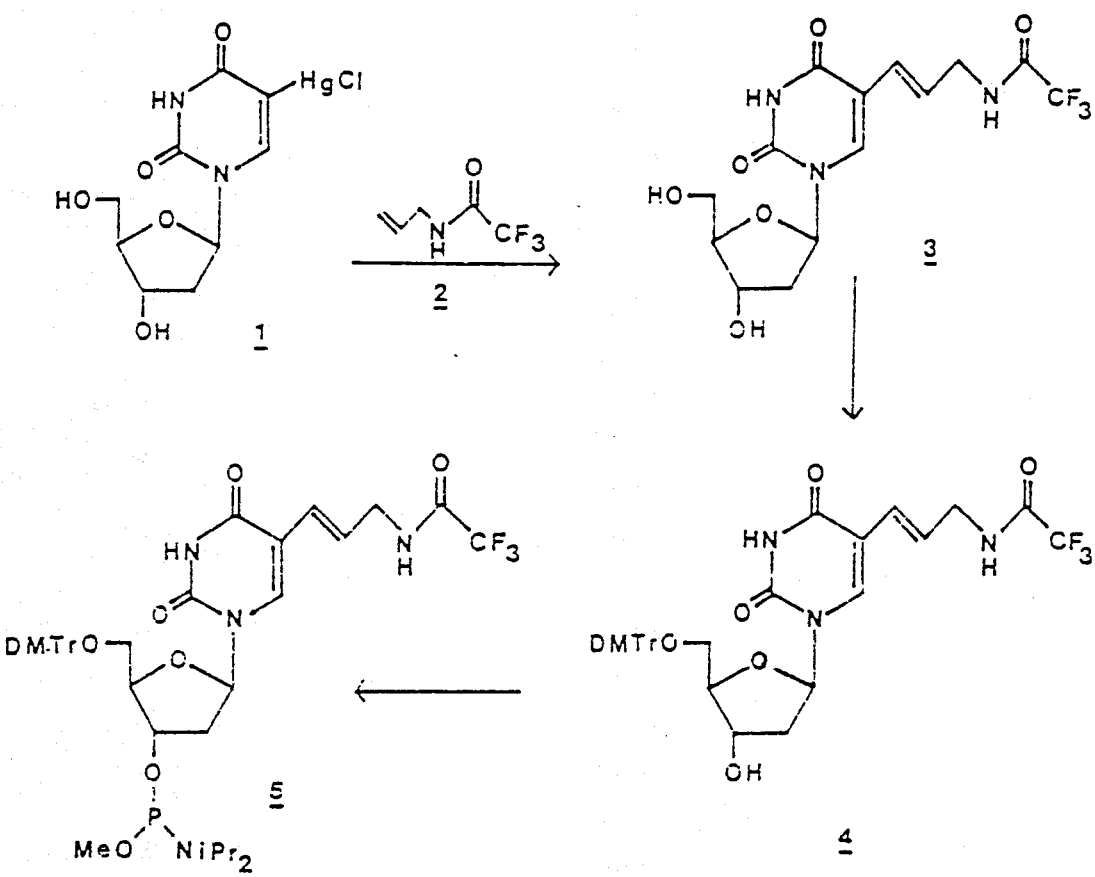
FIG. 1 is a flow chart illustrating the synthesis of 5'-dimethoxytrityl-5-(3-trifluoroacetylaminopropenyl)-2'-deoxyuridine-3'-N,N-diisopropyl methoxy phosphoramidite(compound 5) which is described under Biotinylated Nucleotide Synthesis, below.

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated by this term as used and can be assayed in accordance with the invention.

The term "analyte" refers to any substance, or class of related substances, whose presence is to be qualitatively or quantitatively determined in a sample fluid. The present assay can be applied to the detection of analytes for which there is a specific binding partner and, conversely, to the detection of the capacity of an analyte medium to bind an analyte (usually due to the presence of a binding partner for the analyte in the sample). The analyte usually is an oligo- or polynucleotide, for which a specific binding partner exists or can be provided. The analyte, in functional terms, is usually selected from an RNA or DNA for which a complementary nucleic acid sequence exists or can be prepared.

The term "analyte-specific moiety" refers to any compound or composite capable of recognizing a particular spatial and polar organization of a molecule, i.e., epitopic site, or a particular informational sequence such as a nucleic acid sequence in preference to other substances. In the majority of embodiments the analyte-specific moiety will be a specific binding assay reagent, such as a nucleic acid hybridization assay probe. Analyte-specific moieties of particular interest include DNA hybridization assay oligonucleotide probes, such as those specific for disease-causing organisms, e.g., N. gonorrhoeae or human papilloma virus, or polynucleotide gene sequences which are indicative of genetic disorders, e.g., Tay-Sachs' or retinoblastoma.

The analyte-specific moiety can be attached either directly or through a non-interfering linkage group with other moieties such as biotin or biotin analogues. When attached directly, such attachment can be either covalent or noncovalent. When it is attached through a non-interfering linkage group, this non-interfering linkage group is one which does not substantially interfere with the characteristic ability of the analyte-specific moiety to bind with an analyte. Further, such linkage groups are characterized in that they do not substantially interfere with the energy emission or other characteristics of a moiety to which they are attached. The linkage group can be uncharged or can include one or more charged functionalities. Linkage of the analyte-specific moiety with other moieties can also be accomplished through polymeric compounds. Such compounds will usually display the non-interfering characteristics of the linkage group described above.

Detection of the analyte specific moiety when attached to the analyte can be accomplished by a variety of means employing detectable molecules. Detectable molecules refer to enzymes, fluorochromes, chromogen and the like which can be coupled to the analyte specific moiety either directly or indirectly. As an example, biotin attached to the analyte specific moiety can be detected with a preformed detectable molecule comprising avidin or streptavidin and a biotinylated enzyme. The enzyme of the resultant complex formed between the detectable molecule and the analyte specific moiety can thus serve as the signal reporting moiety of the assay composition.

The following examples illustrate but are not a limitation of the present invention.

In order to study the efficacy of biotin-labeled oligomer probes as a function of the position and the number of biotin residues, a series of oligomers containing biotin-11-dUMP at various positions were synthesized and compared in hybridization/detection studies to oligomers prepared by enzymatic terminal labeling with biotin-11-dUTP and terminal deoxynucleotide transferase. A deoxyuridine phosphoramidite containing a protected allylamino sidearm was synthesized and used to prepare oligonucleotides with allylamino residues at various positions within a 17-base oligonucleotide sequence. Biotin substituents were subsequently attached to the allylamino sidearms by reaction with N-biotinyl-6-aminocaproic acid N-hydroxysuccinimide ester. These oligomers were hybridized to target DNA immobilized on microtiter wells (ELISA plates), and were detected with a streptavidin-biotinylated horseradish peroxidase complex using hydrogen peroxide as substrate and o-phenylenediamine as chromogen. Using this quantitative, colorimetric hybridization/detection procedure, it was found that oligonucleotides containing biotin labels near or at the ends of the hybridizing sequence were more effective probes than oligomers containing internal biotin labels. An additive effect of increasing numbers of biotin-dUMP residues was found in some labeling configurations. The examples provided below detail the experiments and report the results which have been provided in this paragraph.

Unless otherwise stated, chemical reagents were purchased from Aldrich Co. and were used without further purification. Thin layer chromatography was performed using silica gel 60 F 254 plates (Merck), and silica flash column chromatography was performed using silica gel grade 60 (Merck). Methylene chloride was dried by distillation over anhydrous potassium carbonate, and N,N-diisopropylethylamine was purified by distillation. N-biotinyl-6-aminocaproic acid-N-hydroxysuccinimide ester (Enzotin ®) was supplied by Enzo Biochem., Inc. $^1$H nmr spectra were performed on a Nicolet QE 300 instrument, and $^{31}$P spectra were run on a JEOL GX-400 spectrometer.

Detek ® 1-hrp, terminal deoxynucleotide transferase, and biotin-11-dUTP were from Enzo Biochem., Inc. o-Phenylenediamine dihydrochloride (OPD), bovine serum albumin (30% sterile solution), $H_2O_2$, and Triton X-100 were purchased from Sigma. Immulon ® 2 microtiter (ELISA) plates were purchased from Dynatech. Dextran sulfate was obtained from Pharmacia and formamide was from Fluka. Single-stranded bacteriophage target DNA was prepared by standard procedures, see Maniatis, et al., Molecular Cloning, A Laboratory Manual, (1982) and Kadonaga, et al., Nuc. Ac. Res. 13:1733–1745(1985), from supernatants of E. coli JM103 infected with a recombinant of M13 mp18 bacteriophage (the recombinant DNA contained an unrelated 2.5 kilobase insert in the Eco RI site). Control single-stranded target DNA was prepared from wild type (no lac sequences or polylinker sequences) M13-infected cell supernatants.

The buffers used in various steps of the hybridization/detection assays described below were: 1) SSC: 20×SSC is 3M NaCl, 0.3M sodium citrate; 2) SSPE: 20×SSPE is 3.6M NaCl, 0.2M sodium phosphate buffer pH 7.4, and 0.02M ethylenediamine tetraacetic acid (EDTA); 3) Citrate phosphate buffer, pH 6.0: 0.05M citric acid and 0.1M $Na_2HPO_4$ adjusted to pH 6.0; and 4) PBS: 10×PBS is 1.5M NaCl, 0.1M sodium phosphate buffer pH 7.2±0.2.

Biotinylated Nucleotide Synthesis i. Synthesis of Protected Allyamino-deoxyuridine Phosphoramidite Trifluoroacetyl Allylamide (2)

Trifluoroacetic anhydride (56 ml, 397 mmol) is added dropwise with stirring to a 0° C. solution of allylamine (40.5 g, 60 ml, 800 mmol) over a period of 1.5 hr.

The viscous red solution is stored at room temperature overnight, and then partitioned between ethyl acetate and aqueous sodium bicarbonate (500 ml of each). The ethyl acetate layer is washed with aqueous sodium bicarbonate (2×500 ml) and water (2×500 ml), and dried overnight over anhydrous sodium sulphate. After filtration, the solution is evaporated to dryness and distilled in vacuo. Redistillation gives Compound 2 (FIG. 1) as a colorless oil. Yield: 45.2 g (37%). Bp 109° C./10 cm. nmr (CDCl$_3$) d 6.58, br s, 1 NH, 5.86, m,1, CH, 5.3, m, 2, CH$_2$, 4.0, t, 2, CH$_2$N.

Elemental Analysis for C$_5$H$_6$F$_3$NO: Calc.: C 39.22, H 3.95, F 37.23, N 9.15. Found: C 39.00, H 4.18, F 37.50, N 8.91.

5 (3-Trifluoroacetylaminopropenyl)-2'-Deoxyuridine (3)

A suspension of 5-chloromercuri-2'-deoxyuridine (1) (12.6 g, 27.2 mmol) in sodium acetate buffer (0.1N, pH 5) is treated with trifluoroacetyl allylamide (2) (26 g, 175 mmol) followed by a solution of potassium tetrachloropalladate (8.98 g, 27.5 mmol) in water (100 ml). The mixture is stirred at room temperature for 18 hr and then filtered through celite to remove the black precipitate of mercury and palladium. The filtrate is treated with sodium borohydride (3×100 mg) with stirring and again filtered through celite. The filtrate is evaporated to approximately 300 ml, and extracted with ethyl acetate (6×200 ml). The combined ethyl acetate layers are evaporated to dryness and divided into two portions. Each portion is purified by flash column chromatography on silica gel (250 g) using ethyl acetate as solvent, and fractions 95–180 (20 ml fractions) from each column are combined and evaporated to dryness to give Compound(3) as a white crystalline mass, 3.8 g (37%). Recrystallization of a sample from ethyl acetate/hexane gives analytically pure Compound 3 as white crystals, mp 184°–185° C. nmr (Me$_2$SO-d6) d 11.5, s, 1, NH; 9.7, t, 1, NH; 8.1, s, 1, C$_6$H; 6.4, m, 1, CH=; 6.2, m, 2, C$_1$'H, CH=; 5.3, d, 1, C$_3$'OH; 5.1, t, 1, C$_5$'OH; 4.3, m, 1, CH; 3.8–3.9, m, 3, CH, CH$_2$N; 3.6, m, 2, CH$_2$; 2.1, m, 2, C$_2$'H. uv (H$_2$O) max 241 nm, e 7980; 294 nm, e 6830.

5'-Dimethyoxytrityl-5(3-Trifluoroacetylaminopropenyl)-2'-Deoxyuridine(4)

A solution of Compound 3 (570 mg, 1.52 mmol) in anhydrous pyridine (5 ml) was treated with 4,4'-dimethoxytrityl chloride (617 mg, 1.82 mmol) overnight at room temperature. Since thin layer chromatography (TLC; silica., methylene chloride:methanol, 10:1) indicated that starting material was still present, additional dimethoxytrityl chloride (254 mg) was added, and the solution was stored at room temperature for 3 hr. Methanol (1 ml) was added and the solution was evaporated to dryness and pumped in vacuo overnight. The yellow foam was partitioned between methylene chloride and water (70 ml of each) and the methylene chloride layer was washed with water (2×70 ml) and dried over sodium sulphate overnight. The solution was filtered and the filtrate was evaporated to dryness and purified by flash column chromatography on silica (150 g) using methylene chloride:methanol (25:1) as solvent. Tubes 34–50 (20 ml fractions) contained TLC pure material and were combined and evaporated to dryness. The residue was coevaporated with dry benzene (2×5 ml) and dried overnight in vacuo to give Compound 4 (FIG. 1), 593 mg (57%) as a white amorphous solid. nmr (CDCl$_3$) d 7.90, s, 1, C$_6$H; 7.3–7.5, m, 9, aromatics; 6.89, d, 4, aromatics; 6.44, m, 2, C$_1$'H, CH=; 5.32, d, 2, CH=; 4.65, s, 1, CH; 4.14, s, 2, CH$_2$N; 3.83, s, 6, OCH$_3$; 3.7, m, 1, CH; 3.54, m, 2, C$_5$'H; 2.42, m, 2, CH$_2$.

5'-Dimethoxytrityl-5(3-Trifluoroacetylaminopropenyl)-2'-Deoxyuridine-3'-N,N-Di-Isopropyl-Methoxy-Phosphoramidite (5)

A solution of Compound 4 (340 mg, 0.5 mmol) in dry methylene chloride (4 ml) in a septum sealed flask was treated with N,N-diisopropylethylamine (0.286 ml, 1.5 mmol) followed by chloro-N,N-diisopropylaminomethoxyphosphine (0.145 ml, 0.75 mmol) both reagents being added via syringe. The solution was stored at room temperature for 20 min., and partitioned between water and ethyl acetate (25 ml of each). The ethyl acetate layer was washed with aqueous sodium bicarbonate (1×25 ml), water (1×25 ml), and dried over anhydrous magnesium sulphate overnight. The solid was filtered off and the filtrate was evaporated to dryness, coevaporated with dry benzene (2×5 ml), and dried in vacuo overnight. The residue was precipitated by dissolution in dry benzene (2.5 ml) and addition to a vigorously stirred 0° C. solution of dry hexane. The precipitate was collected by filtration, washed with cold hexane (6×20 ml), and dried in vacuo overnight to give Compound 5 (FIG. 1) as a white amorphous solid, 311 mg (74%). $^{31}$P nmr (CDCl$_3$) d 149.44, 148.91, impurity at d 8.37. tlc (CH$_2$Cl$_2$/MeOH, 20:1) Rf 0.4, impurity at Rf 0.2.

ii. Oligonucleotide Synthesis

Oligonucleotides were synthesized by the phosphoramidite method on an Applied Biosystems Co. instrument, model 380 B, using methyl phosphoramidites and reagents as supplied by the manufacturer. Both 0.2 μmol and 1 μmol synthesis cycles were employed. The modified phosphoramidite (Compound 5) was dissolved in dry acetonitrile and filtered through a glass wool plug immediately before loading onto the machine. Phosphoramidite additions were monitored by release of trityl cation, and the modified Compound 5 was incorporated to the same extent as the unmodified phosphoramidites. The nucleotide sequence of the oligonucleotides synthesized as reported here is set forth in Example 1, Table 1, below. After completion of the synthesis, the oligomers were deprotected by treatment with ammonia at 55° C. overnight, which also served to cleave the trifluoroacetyl groups to produce oligonucleotides with allylamino sidearms at the selected positions.

iii. Biotinylation of Oligonucleotides

Crude oligonucleotides, prepared as described above, were initially purified by passage through a Sephadex G 25 column (1×16 cm) using 20 mM triethylammonium bicarbonate pH 7 (TEAB) as the eluting buffer. Fractions 4–6 (1 ml fractions) were collected, evaporated to dryness, dissolved in water, and assayed by uv spectroscopy. An aliquot (20 OD$_{260}$ units) in water (100 μl) of each of the purified oligonucleotides was combined with 0.1M sodium borate (600 μl) followed by addition of dimethylsulfoxide (150 μl). The resulting solution was combined with a freshly prepared solution of N-biotinyl-6-aminocaproic acid-N-hydroxysuccinimide ester (5 mg) in dimethylsulfoxide (125 μl), and the resulting reaction mixture was incubated at room temperature overnight. Then, the resultant reaction mixture was divided into two portions and each was purified by passage through a Sephadex G 25 column (1×16 cm) equilibrated with 20 mM TEAB. With respect to each oligonucleotide, fractions 4–6 (1 ml fractions) from each of the two columns run in parallel were combined and evaporated to give the crude biotinylated oligomer, which was then purified by gel electrophoresis as described below.

iv. Purification of Biotinylated Oligomers by Gel Electrophoresis

The biotinylated oligomers, prepared as described above, were further purified by 20% polyacrylamide gel electrophoresis (containing acrylamide:bisacrylamide, 40:1 and 7M urea) on 0.4 mm thick gels. Thereafter, 20 OD$_{260}$ units of each biotinylated oligonucleotide were dissolved in 100 μl of a solution containing 0.09M Tris base, 0.09M boric acid, 0.25M EDTA (1×TBE), 40% formamide and 0.25% bromophenol blue. Each oligonucleotide solution was applied to twenty 8 mm wells, and electrophoresed at 30 milliamps in 1×TBE buffer for 3-4 hrs. The bands were visualized with a short wave uv lamp, using a sheet of silica gel 60 F 254 (Merck) as background. The product band, which was the most slowly migrating band, was cut out and immersed in 100 mM Tris base, 0.5M NaCl, 5 mM EDTA, pH 8, for 18 hrs at 60° C. This solution was decanted and desalted using a Sep-Pak cartridge (Millipore). The solution was loaded onto the cartridge, washed with water (20 ml) to remove salts, and the oligomer was eluted with methanol/water, 1:1 (3 ml). After evaporation to dryness, the residue was applied to a Sephadex G 25 column (1×16 cm) using 20 mM TEAB as the eluting buffer. The fractions containing oligonucleotide were combined, evaporated to dryness, and dissolved in water (1 ml) to provide a stock solution suitable for use in the hybridization experiments reported below.

v. Preparation of Terminal Biotin-Labeled Oligomer Probes

The unmodified oligomer prepared for this study was terminal labeled using terminal deoxynucleotide transferase in reactions containing 0.2M potassium cacodylate buffer pH 7.2, 1 mM CoCl$_2$, terminal transferase (20 units/μg of oligomer), oligomer (at 20 μg/ml) and biotin-11-dUTP at a concentration giving a ratio of nucleotide to oligomer varying from 5:1 to 50:1. In some cases, $^3$H-TTP was added to monitor the incorporation of biotin-11-dUTP, Brakel, et al., in Kingsbury, D. T. and Falkow, S. (Eds.), Rapid Detection and Identification of Infectious Agents, Academic Press, New York, pp. 235–243 (1985). In other cases, TTP was added to the reactions in order to separate, or alternate with, the biotin-11-dUTP in the terminal addition. Reactions were allowed to proceed for 90 minutes at 37° C. and were terminated by the addition of EDTA to a concentration of 25 mM. The terminal labeled oligomers were used in the hybridization/detection experiments reported below without further purification.

Hybridization-Detection Assay Procedures

The fixation of target nucleic acids to Immulon® 2 microtiter plates was accomplished by a modification of procedures described by Nagata, et. al., FEBS Letters 183; 379-382 (1985). The procedure used was as follows. The plates were first rinsed with 1M ammonium acetate and the target DNAs were added to the wells at an appropriate concentration in a volume of 50 μl of 1M ammonium acetate. Single stranded target DNAs were loaded into wells without prior treatment other than dilution into 1M ammonium acetate. The loaded plates were allowed to incubate for 1.5-2 hrs at 37° C. in order to fix the target DNAs to the plate. The plates were either used immediately after preparation or were stored at 4° C. prior to use for hybridization experiments. Just prior to hybridization, the plates were rinsed twice with 2×SSC and once with 2×SSC containing 1% (v/v) Triton X-100.

Hybridizations were carried out at room temperature using 100 μl of solutions containing 30% (v/v) formamide, 2× or 4×SSPE, 1% (v/v) Triton X-100, 5% (w/v) dextran sulfate, and probe DNA. The oligonucleotide probes were used at a final concentration of 100 ng/ml. The hybridizations were allowed to proceed for 30 to 90 minutes.

Following the hybridization incubation, the plates were emptied by inversion and washed, usually with 0.2×SSC containing 0.1% Triton X-100. Washing consisted of filling the wells of the plates with 200 μl of solution followed by inversion of the plate after gentle shaking for 5-10 seconds (or longer, up to one to two minutes, if several plates were processed at one time). In some cases washes were performed with buffers that were heated to 37°-42° C., to provide conditions of sufficient stringency to perform hybrid melting experiments. Following 4 to 5 washes, the biotin in the hybridized probe was detected as follows.

The hybridized, biotinylated probe DNAs were detected by use of a Detek® 1-hrp complex of streptavidin and biotinylated horseradish peroxidase as follows. The complex was diluted into 1×PBS, 0.5M NaCl, 0.1% BSA, 0.1% Triton X-100, 5 mM EDTA (complex dilution buffer) and added to the wells of the plate (50 μl per well). The complex was incubated in the wells for 30 minutes at room temperature, unless otherwise noted. The plates were then washed twice with complex dilution buffer and three times with 1×PBS containing 5 mM EDTA. The horseradish peroxidase in the bound detection complex was reacted (20-30 minutes at room temperature) in the dark with reaction mixture (150 μl per well) containing H$_2$O$_2$ (0.0125%) and OPD (1.6 mg/ml) in citrate/phosphate buffer, pH 6.0. Color development was terminated by addition of 4N H$_2$SO$_4$ (50 μl per well). Optical density measurements (at 490 nm) were made within 5 to 10 minutes of termination of the reactions using an Interlab microplate reader model NJ 2000. Wells that had received only 1M ammonium acetate during the DNA fixation procedure, but which had been exposed to probe, detection complex, and peroxidase reaction mixture were used as zero (blank) controls for the absorbance readings. All hybridizations were performed in duplicate to quadruplicate for the various determinations. Absorbance readings from hybridization in wells containing non-complementary target DNA (wild type bacteriophage DNA) ranged from 0.010 to 0.050 and were subtracted from the absorbance readings reported for hybridization to complementary target DNA. Changes in and variations of these procedures are described in the individual experiments reported below, where applicable.

EXAMPLE 1

The heptadecanucleotide (17 base) sequence complementary to bases 6204 to 6220 (part of the E. coli lac gene) of bacteriophage M13 mp series DNA was selected for modification. This sequence and the various biotin-labeled oligonucleotides that were synthesized along with the results of the hybridization/detection experiments are shown in Table 1 as follows.

TABLE 1

| OLIGOMER | SEQUENCE | RELATIVE SIGNAL STRENGTH |
|---|---|---|
| 6 |        B<br>GTCATAGCUGTTTCCTG | 0.11 |
| 7 |          B<br>GTCATAGCTGTTUCCTG | 0.16 |
| 8 |              B<br>GTCATAGCTGTTTCCUG | 0.68 |
| 9 | B<br>U—GTCATAGCTGTTTCCTG | 1.00 |
| 10 |     B     B<br>GTCAUAGCTTUCCTG | 0.47 |
| 11 | B          B<br>GUCATAGCTGTTUCCTG | 0.91 |
| 12 | B             B<br>GUCATAGCTGTTTCCUG | 1.25 |
| 13 |               B  B<br>GTCATAGCTGTTTCCTG—U—U—T | 2.14 |
| 14 | B      B       B<br>GUCATAGCUGTTTCCUG | 1.12 |
| 15[S] |               B  B  B<br>GTCATAGCTGTTTCCTG—U—U—U | 3.08 |

B<br>
U biotinylated dUMP

By the oligonucleotide synthesis procedure previously described, single biotin substitutions were introduced at internal sites (oligomers 6 and 7), and close to the 3'-terminus (oligomer 8). An octadecamer containing the basic sequence with an addition of a single biotinylated nucleotide at the 5'-terminus was also synthesized (oligomer 9). The 5'-terminal base of this oligomer cannot hybridize to the target M13 DNA due to non-complementarity, and therefore acts as a small tail. Oligomers containing two biotins per sequence were also synthesized, such as 10, which contains two biotins at internal sites, and 11 which contains one biotin close to the terminus, and one at an internal site. Oligomer 12 possesses biotins close to the termini of the molecule, and oligomer 13 is a dodecamer in which the basic sequence was extended by the addition of three nucleotides (two biotinylated residues and one terminal thymidine residue) at the 3'-terminus. Since the polymer-supported method of synthesis requires a 3'-terminal base of the desired sequence that is already attached to the solid support, and since the modified trifluoroacetylaminopropenyl nucleotide attached to the solid support was not available, a thymidine residue at the 3'-terminal position was used. One oligomer containing three biotin groups (oligomer 14) was also synthesized. Finally, the unmodified oligomer was synthesized and was labeled by terminal addition of biotin-11-dUTP using terminal deoxynucleotide transferase to give oligomer 15, containing 3 to 4 biotin-dUMP residues per molecule (calculated labeling of 3.3 nucleotides per oligomer).

Because the assay procedures used in this study were substantially different from those used for hybridization of labeled oligomers to membrane-bound target DNA, some of the differences in slopes of the hybridization-detection curves could have resulted from differences in the stabilities of the hybrids and not from differences in the accessibility of the biotin label to detection. To eliminate this possibility, we initially used standard membrane-bound target DNA techniques, as shown in Wallace, et al, Nucleic Acids Res. 6: 3543-3557 (1979), to assess the hybridization sensitivity of several of the oligomers after $^{32}$P labeling with polynucleotide kinase and $^{32}$P-ATP. Oligomers 6, 7, 10, 12, and 14 (Table 1) were labeled and then hybridized to decreasing amounts of M13mp18 (single-stranded) DNA fixed on nitrocellulose filters. Under conditions of moderate stringency, the radiolabeled oligomers hybridized with equal sensitivity to the membrane-bound target DNA. These results indicated that, when detection was based on radioactivity, the biotin labels had no effect on the hybridization sensitivity of the oligomers.

Figure 2:
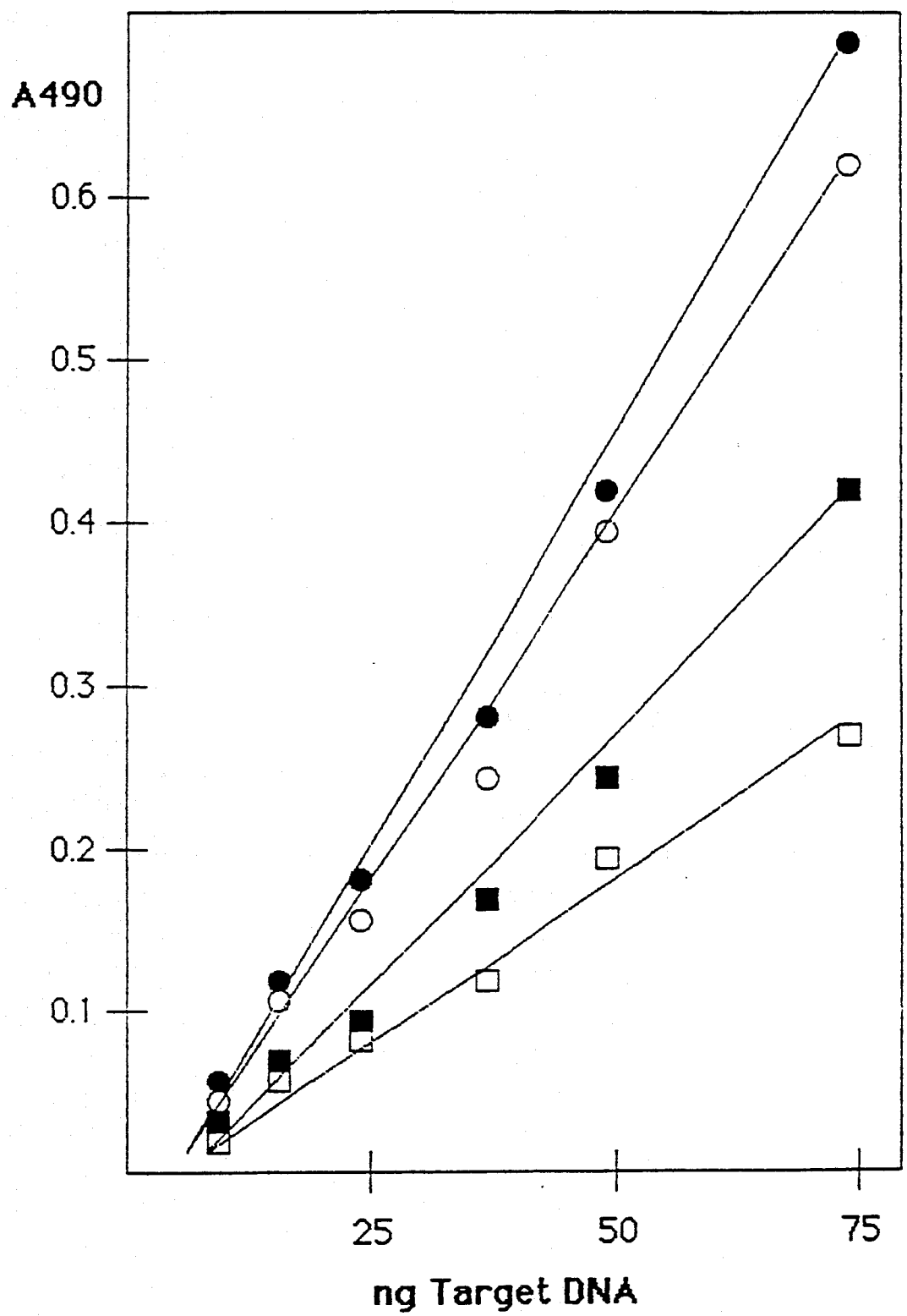
FIG. 2 is a sensitivity curve showing the signal output obtained after hybridization-detection in microtitre plates with oligomers labelled with biotin at various positions in the nucleotide sequence. Results are shown for oligomers 12 ( ), 9 (O), 8 and 10 ( ).

Microtiter plate hybridization procedures were used with biotinylated DNA probes. The procedures for use with oligomeric probes were as described above. In order to compare the results of hybridization/detection obtained with the various oligomer probes, a standard hybridization sensitivity experiment was performed in which a different amount of DNA target is provided in each well. Samples of each oligomeric probe were hybridized to decreasing amounts of target DNA. Following detection of the hybridized biotin-labeled oligomers with streptavidin-biotinylated horseradish peroxidase, the slopes of the curves of absorbance at 490 nm versus ng of target DNA were calculated by linear regression. The results from such standard hybridization sensitivity experiments with oligomers 8, 9, 10, and 12 are shown in FIG. 2.

All of the oligomer probes prepared for this study generated signals that were directly proportional to the amount of target DNA. The correlation coefficients of the curves ranged from 0.995 to 0.999. The results of hybridization/detection with the various oligomers differed from each other only in the slopes of the curves as determined by linear regression.

The results of the hybridization/detection sensitivity experiments for the chemically synthesized oligomers and one enzymatically labeled oligomer were summarized in Table 1, supra. The slopes of the hybridization detection curves were normalized to the slope of the curve obtained with oligomer 9 (the actual slope for oligomer 9 ranged from 0.005–0.010 A490 units/ng of target bacteriophage DNA in various determinations). The values shown are the averages of values obtained in at least three determinations for each oligomer. A comparison of the oligomers containing a single biotin-modified nucleotide (6, 7, 8, and 9) showed that as the biotin-labeled nucleotide was moved from the center of the hybridizing region of the oligomer probe to near the terminus of the molecule, the signal strength (A490/ng of target DNA) increased. There was a six-fold difference between the slopes of the curves generated by oligomer 6 (biotin in the center of the molecule) and oligomer 8 (biotin located on the penultimate nucleotide of the hybridizing sequence). This trend was also observed for the oligomers containing two biotin-modified nucleotides (10, 11, 12, and 13). The weakest signal was generated by the oligomer containing two internal biotins (oligomer 10) and the strongest signal was generated by the oligomer containing biotins on the 3'- and 5'-penultimate nucleotides (oligomer 12). The signal from the two biotin-dUMP molecules in oligomer 12 was about double that of the single biotin-dUMP in oligomer 8 (relative signals of 1.25 and 0.68, respectively), demonstrating that biotin molecules located near the termini of the hybridizing region produce additive signals. The addition of a third, centrally located biotin-dUMP (oligomer 14) did not increase the signal strength but, rather, the signal generated by this oligomer was either the same as or, on the average, slightly less than that generated by the double-labeled oligomer 1

EXAMPLE 2

Figure 3:
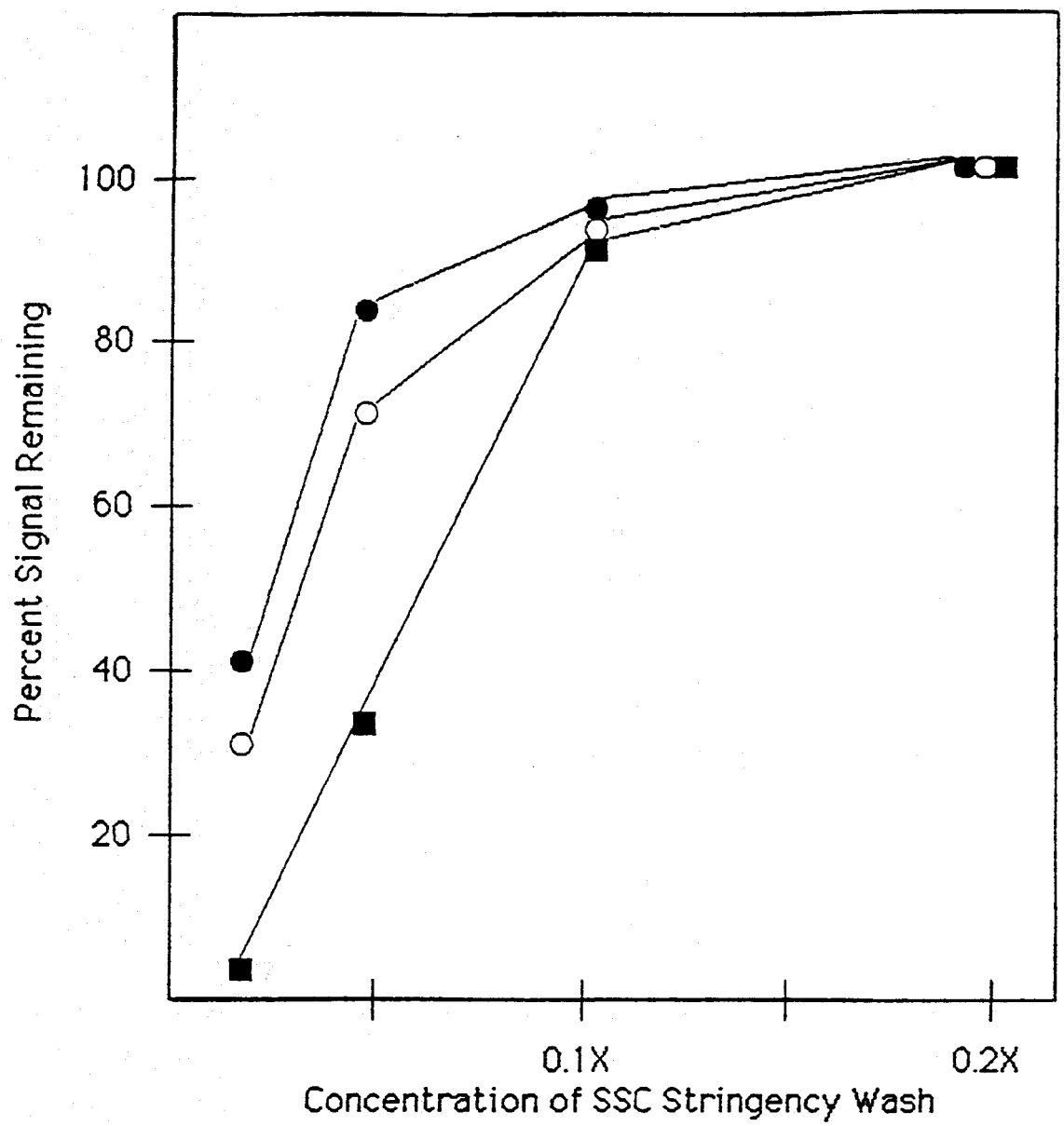
FIG. 3 depicts the stability of biotinylated oligomer-target DNA hybrids to washing with various concentrations of SSC. Results are shown for oligomers 9 ( ), 12 ( ), and 14 ( ).

The experiments described here were performed to determine whether the stringency of the washes following hybridization were affecting the results of the hybridization/detection. The effect of increasing the stringency of the hybridization washes is shown in FIG. 3 for oligomers 9, 12, and 14, and the results of this hybrid stability experiment are summarized for all of the chemically synthesized oligomers in Table 2.

TABLE 2

| Oligomer | Percent Signal Remaining after Stringency Wash in: | | |
|---|---|---|---|
| | 0.02 × SSC | 0.05 × SSC | 0.10 × SSC |
| 6 | <10 | 43 | 94 |
| 7 | <10 | 46 | 93 |
| 8 | 42 | 79 | 100 |
| 9 | 40 | 83 | 96 |
| 10 | <10 | 48 | 95 |
| 11 | 33 | 70 | 98 |
| 12 | 27 | 70 | 95 |
| 13 | 21 | 81 | 99 |
| 14 | <10 | 32 | 90 |

These results show that all of the probe: target DNA hybrids were stable (90–100% of maximum signal) to washing in 0.1×SSC at 37°–42° C. but did have demonstrably different stabilities when conditions were changed. The least stable were those in which the hybridizing sequence of the oligomer contained internal and relatively closely-spaced biotins. The oligomer forming the least stable hybrid was oligomer 14, while the most stable and superior hybrids were formed by oligomers 8 and 9. Thus, oligomers containing biotin substituted nucleotides at the 3' and/or 5' ends were found to have superior stability compared to those with internal substitutions.

EXAMPLE 3

Because the oligomer prepared by enzymatic terminal addition of biotin-11-dUTP (oligomer 15) generated the strongest signal, the decision was made to examine the effect of tail length, numbers of biotins, and biotin spacing on hybridization/detection using other preparations of enzyme-labeled oligomer, as shown in Table 3.

TABLE 3

| Oligomer Preparation | Length of "Tail" | Number of Biotins | Relative Signal | |
|---|---|---|---|---|
| | | | 30 min. | 3 hrs. |
| 9 | 1 | 1 | 1.0 | 1.0 |
| 13 | 3 | 2 | 1.9 | 1.3 |
| A | ≈1 | ≈1 | 1.4 | 1.1 |
| B (=15) | 3–4 | 3–4 | 2.8 | 1.6 |
| C | 8 | 8 | 5.9 | 2.8 |
| D | 12 | 12 | 7.2 | 2.9 |
| E | 17 | 17 | 8.0 | 3.7 |
| F [4:1] | 23 | 18 | 8.7 | 3.6 |
| G [1:1] | 23 | 12 | 7.6 | 3.3 |
| H [1:4] | 21 | 4 | 3.0 | 1.2 |
| I [1:9] | 17 | ≈2 | 2.4 | 0.95 |

Oligomers with terminal extensions were prepared chemically or by addition of biotin-11-dUTP with terminal transferase. Oligomers A–E were prepared with only biotin-11-dUTP in the reaction mixtures and F–I were prepared with different mixtures of biotin-11-dUTP and TTP. The ratio of biotin-11-dUTP to TTP is indicated by the values in the brackets. The lengths of the terminal additions were determined by monitoring 3H-TTP incorporation and the number of biotin-dUMP molecules per addition were calculated. The oligomers were hybridized and detected following either a 30 min. or a 3 hour incubation with detection complex as described within. The results were calculated and normalized to the results for oligomer 9 for each detection complex incubation time.

Results obtained in standard assays (30 minute incubation with detection complex, Table 3) with oligomers labeled to different extents with only biotin-11-dUTP (preparations A–E) showed that the signal strength of the probe was directly related to the number of biotin-11-dUMP residues in the terminal addition. The signal strength increased regularly over the range of the terminal additions generated by this labeling method but the effect of each additional biotin-11-dUMP residue decreased as the number of biotin-dUMP residues was increased from about 4–8 to 12 and 17. The signal per biotin values decreased from close to unity for 9, 13, A, and B (=15) to values of 0.6 and 0.4 for preparations D and E, respectively. When oligomers that were labeled with different ratios of biotin-11-dUTP to TTP in the terminal transferase reactions (preparations F–I, 30 minute incubation, Table 3) were compared, a similar trend in signal per biotin values was observed. As the number of biotin-dUMP residues increased, the signal strength increased, but the signal per biotin values decreased. Because the increased signal strength of the terminal labeled preparations was expected to be in part a function of the kinetics of binding of the detection complex, the results described above were compared with those obtained after extended (3 hour) incubations with detection complex. When the detection complex was allowed to bind for 3 hours, preparations E and F generated signals (slopes) only 3.6–3.7 times greater than that of oligomer 9 rather than 8–8.7 times greater, suggesting that at equilibrium, 3–4 times as many detection complexes bind to the 17–18 biotin-dUMP residues available on these terminally labeled oligomers than bind to the single biotin-dUMP residue on oligomer 9. A surprising result of these kinetic studies was that the signals generated by some preparations co-labeled with TTP (H and I) were reduced relative to oligomer 9, being only 1.2 and 0.95 times the signal of oligomer 9, rather than 3 and 2.4 times, respectively. These results suggest that the availability of the biotin residues decreased with time in terminal extensions containing primarily TMP rather than primarily biotin-dUMP.

The most effective site for introduction of biotin labels was outside the hybridizing sequence, i.e., as "tails" extending from either the 5' or the 3' termini. The chemically synthesized oligonucleotide probes were compared to probes prepared by terminal labeling with terminal transferase (2,3), and the results of these comparisons substantiate the conclusion that external biotin-dUMP residues are the most readily detectable. Although some of the signaling differences among the "tailed" oligomers were shown to result from favorable kinetics of binding of detection complex, the differences were not entirely eliminated by allowing the binding of detection complex to approach equilibrium. As the binding of detection complex approached equilibrium, the biotin-dUMP residues in the terminal extensions signaled more like internal biotin-dUMP residues. Nevertheless, the terminally labeled oligonucleotides were still more sensitive probes than those labeled internally with one to three biotin-dUMP's. Attempts to separate the terminal biotin-dUMP residues by co-labeling with TTP did not appear to generate a more favorable labeling configuration. It is possible that the structure of these terminal extensions is more folded and the biotin residues are less accessible than in the terminal extensions containing solely or primarily biotin-dUMP. The oligomers containing multiple terminal biotins described above were labeled enzymatically, however, synthetic labeling at the 3'- or the 5'-termini by the procedures described within have duplicated the enzymatic labelings. Thus, multiple labelings at both the 3' and the 5' termini of oligonucleotides generate synthetic probes that are more sensitive than those labeled with single biotins at the 3' and 5' termini.

EXAMPLE 4

A polymeric compound, such as dextran, is first polybiotinylated and then used as a non-interfering linkage group. Such a compound is attached to a hybridized probe via avidin or streptavidin. Thereafter, signal generation is effected with addition of the Detek ® 1-hrp signal generating system. This system amplifies the resultant signal 10 to 100 fold compared to direct detection with Detek ® 1-hrp signal generating system applied directly to the biotinylated probe.

What is claimed is:

1. An oligo- or polynucleotide having at least one non-radioactive moiety directly or indirectly attached to each of the 5' and 3' end nucleotides thereof.

2. The oligo- or polynucleotide of claim 1 wherein said non-radioactive moiety comprises biotin or a biotin analogue.

3. The oligo- or polynucleotide of claim 2 comprising at least two molecules of said biotin or biotin analogue attached to at least one end thereof.

4. The oligo- or polynucleotide of claim 3 comprising from about two to about eighteen molecules of said biotin or biotin analogue attached to at least one end thereof.

5. The oligo- or polynucleotide of claim 2 comprising at least two molecules of said biotin or biotin analogue attached at each end thereof.

6. The oligo- or polynucleotide of claim 5 comprising from about two to about eighteen molecules of said biotin or biotin analogue at each end thereof.

7. The oligo- or polynucleotide of claim 2 wherein at least one molecule of said biotin or biotin analogue is attached to the terminal nucleotide through a non-interfering linkage group.

8. The oligo- or polynucleotide of claim 7 wherein said biotin attachment comprises biotin-11-dUMP.

9. The oligo- or polynucleotide of claim 7 wherein said biotin attachment comprises biotin-11-allylamine-dUMP.

10. The oligo- or polynucleotide of claim 2 wherein at least one of said end nucleotides is attached to a biotinylated polymer.

11. The oligo- or polynucleotide of claim 10 wherein said biotinylated polymer comprises poly biotinylated dextran.

12. An oligo- or polynucleotide having at least one non-radioactive moiety directly or indirectly attached to each of the 5' and 3' terminal nucleotides external to a target hybridization region of said oligo- or polynucleotide.

13. The oligo- or polynucleotide of claim 12 wherein said non-radioactive moiety comprises biotin or a biotin analogue.

14. A nucleic acid hybridization assay composition comprising an oligo- or polynucleotide of claims 1 or 12, and a preformed detectable molecular complex.

15. A nucleic acid hybridization assay composition comprising an oligo- or polynucleotide of claims 2, 3, 4, 5, 6, 7, 8, 9, 11 or 13, and a preformed avidin or streptavidin detectable molecular complex.

16. The composition of claim 15 wherein said detectable molecular complex is selected from a fluor, chromogen, enzyme, phosphor, electron dense reagent, or a combination of any of the foregoing.

17. The composition of claim 16 wherein said enzyme is selected from peroxidase, alkaline phosphatase, acid phosphatase, beta-galactosidase, and glucose oxidase, or a combination of any of the foregoing.

18. A method for detecting a target nucleic acid sequence in a sample comprising:
rendering the nucleic acid in said sample in single-stranded form;
contacting said single-stranded nucleic acid under hybridizing conditions with (i) an oligo- or polynucleotide probe having at least one non-radioactive moiety directly or indirectly attached to each of the 5' and 3' end nucleotides thereof, said probe being capable of hybridizing to said target nucleic acid sequence, and (ii) a preformed detectable molecular complex; and
detecting any hybridized complexes, thereby detecting the target nucleic acid sequence.

19. The method of claim 18 wherein the attachment of said non-radioactive moiety to the oligo- or polynucleotide probe is external to a target hybridization region of said probe.

20. The method of claim 18 wherein said non-radioactive moiety of the oligo- or polynucleotide probe comprises biotin or a biotin analogue.

21. The method of claim 20 wherein said oligo- or polynucleotide probe comprises at least two molecules of said biotin or biotin analogue attached to at least one end thereof.

22. The method of claim 21 wherein said probe comprises from about two to about eighteen molecules of said biotin or biotin analogue attached to at least one end thereof.

23. The method of claim 20 wherein said oligo- or polynucleotide probe comprises at least two molecules of said biotin or biotin analogue at each end thereof.

24. The method of claim 23 wherein said probe comprises from about two to about eighteen molecules of said biotin or biotin analogue at each end thereof.

25. The method of claim 20 wherein at least one of said biotin or biotin analogue molecules in said probe is attached to the terminal nucleotide through a non-interfering linkage group.

26. The method of claim 25 wherein said biotin attachment comprises biotin-11-dUMP.

27. The method of claim 25 wherein said biotin attachment comprises biotin-11-allylamine-dUMP.

28. The method of claim 18 wherein at least one of said end nucleotides in the probe is attached to a biotinylated polymer.

29. The method of claim 28 wherein said biotinylated polymer comprises poly biotinylated dextran.

30. The method of claim 20 wherein said detectable molecular complex comprises avidin or streptavidin.

31. The method of claims 18 or 30 wherein said detectable molecular complex is selected from a fluor, chromogen, enzyme, phosphor, electron dense reagent, or a combination of any of the foregoing.

32. The method of claim 31 wherein said enzyme is selected from peroxidase, alkaline phosphatase, acid phosphatase, beta-galactosidase, and glucose oxidase, or a combination of any of the foregoing.

* * * * *